United States Patent [19]

Parker

[11] 4,032,647
[45] June 28, 1977

[54] SUBSTITUTED THENOYLACETIC ACID AND ESTERS

[75] Inventor: Roger Alan Parker, Cincinnati, Ohio

[73] Assignee: Richardson-Merrell Inc., Wilton, Conn.

[22] Filed: June 16, 1975

[21] Appl. No.: 587,117

[52] U.S. Cl. .................. 424/275; 260/239 BF; 260/247.1 P; 260/268 H; 260/293.57; 260/294.8 D; 260/326.84; 260/329 S; 260/329 AM; 260/332.2 A; 260/332.3 R; 424/244; 424/248.51; 424/250; 424/267; 424/274

[51] Int. Cl.² .................. A01N 9/00; C07D 333/16

[58] Field of Search .......... 260/332.2 R, 332.2 A, 260/332.3 R, 294.8 D; 424/275

[56] References Cited

UNITED STATES PATENTS 3,795,681 3/1974 Ruchig et al. ............ 424/275

Primary Examiner—James O. Thomas, Jr.
Assistant Examiner—A. Siegel
Attorney, Agent, or Firm—L. Ruth Hattan; G. W. Rauchfuss, Jr.; E. O. Retter

[57] ABSTRACT

Substituted thenoylacetic acid and esters, and pharmaceutically acceptable salts thereof of the following general formula are useful as hypolipidemic agents:

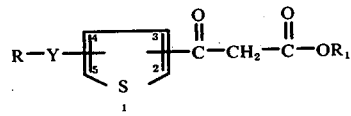

wherein Y is selected from oxygen and divalent sulfur; R is selected from a straight or branched saturated hydrocarbon chain containing from 10 to 20 carbon atoms and a straight or branched unsaturated hydrocarbon chain containing from 10 to 20 carbon atoms and from 1 to 4 double bonds; $R_1$ is selected from hydrogen and an ester group.

12 Claims, No Drawings

SUBSTITUTED THENOYLACETIC ACID AND ESTERS

FIELD OF INVENTION

This invention relates to substituted thenoylacetic acid and esters and pharmaceutically acceptable salts thereof and their use as hypolipidemic agents.

SUMMARY OF INVENTION

Compounds of the following general Formula 1 are useful as hypolipidemic agents:

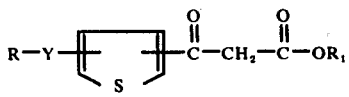

Formula 1 wherein Y is selected from oxygen and divalent sulfur; R is selected from a straight or branched saturated hydrocarbon chain containing from 10 to 20 carbon atoms and a straight or branched unsaturated hydrocarbon chain containing from 10 to 20 carbon atoms and from 1 to 4 double bonds; $R_1$ is selected from hydrogen, a straight or branched lower alkyl chain of from 1 to 6 carbon atoms, benzyl, phenethyl, pyridylmethyl, and Z; Z is selected from A. the group

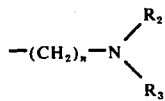

wherein n is the integer 2 or 3; $R_2$ is selected from a straight or branched lower alkyl chain of from 1 to 4 carbon atoms and alkylcarbonyl wherein the alkyl moiety contains from 1 to 4 carbon atoms; $R_3$ is selected from hydrogen and a straight or branched lower alkyl chain of from 1 to 4 carbon atoms with the proviso that when $R_3$ is hydrogen, $R_2$ is alkylcarbonyl, or, when $R_2$ is other than alkylcarbonyl, $R_2$ and $R_3$ taken together with the nitrogen atom to which each is attached forms a monocyclic heterocyclic group selected from pyrrolidino, piperidino, morpholino, and piperazino; and B. the group

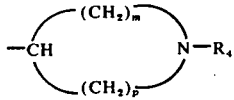

wherein the sum of the integers as represented by m and p is equal to from 3 to 5; and $R_4$ is a straight or branched lower alkyl chain of from 1 to 4 carbon atoms.

Pharmaceutically acceptable salts of compounds of Formula 1 wherein $R_1$ represents hydrogen or a basic group are also included within the scope of this invention.

DETAILED DESCRIPTION OF INVENTION

In the above general Formula 1, the substituent group represented as R—Y— and the β-oxopropionic acid function may each be attached at any of the positions 2-, 3-, 4-, or 5- of the thiophene ring with the proviso that both the R—Y— group and the β-oxopropionic acid function are not attached to the same carbon atom.

The substituent R may be a straight or branched saturated hydrocarbon chain containing from 10 to 20 carbon atoms in which case the R—Y— group may be represented as $C_qH_{2q+1}$-Y— wherein Y is oxygen or sulfur, q is an integer of from 10 to 20, and the hydrocarbon chain may be straight or branched. The substituent group R may also be an unsaturated hydrocarbon chain containing from 10 to 20 carbon atoms and from 1 to 4 double bonds in which case the R—Y— group may be represented as $C_qH_{2q-z}$—Y— wherein Y is oxygen or sulfur, q is an integer of from 10 to 20, z is the integer 1, 3, 5 or 7, as the number of double bonds varies from 1 to 4 respectively, and the hydrocarbon chain may be straight or branched.

Illustrative examples of straight or branched saturated hydrocarbon chains which R may represent are, for example, decyl, undecyl, dodecyl, tridecyl, tetradecyl, 3,7-dimethyloctyl, 2,4-diethylnonyl, 1-methylundecyl, pentadecyl, hexadecyl, heptadecyl, 3-methyloctadecyl, nonadecyl, and didecyl.

Illustrative examples of straight or branched unsaturated hydrocarbon chains containing from 1 to 4 double bonds which R may represent are, for example, 10-undecenyl, 9,12-octadecyldienyl, 3,7,11-trimethyl-2,6,10-hexadecyltrienyl, 3,7-dimethyl-2,6-octadienyl, 5,9-dimethyl-2,4,8-decatrienyl, 4,6-dimethyloct-3-enyl, 1,2,5,9-tetramethyl-2,4,8-decatrienyl, and 11-didecenyl. Both cis- and trans-isomers of the unsaturated hydrocarbon chains are included within the scope of this invention.

Illustrative examples of straight or branched lower alkyl chains of from 1 to 6 carbon atoms which $R_1$ may represent are, for example, methyl, ethyl, n-propyl, isopropyl, n-butyl, tert-butyl, pentyl and hexyl.

Illustrative examples of straight or branched lower alkyl chains of from 1 to 4 carbon atoms which $R_2$, $R_3$ and $R_4$ may represent are, for example, methyl, ethyl, n-propyl, isopropyl, n-butyl, and tert-butyl.

The term alkylcarbonyl is taken to mean the group

wherein the alkyl moiety contains from 1 to 4 carbon atoms, for example, methyl, ethyl, n-propyl and n-butyl.

Pharmaceutically acceptable salts of the compounds of general Formula 1 wherein $R_1$ represents hydrogen are those formed with any suitable inorganic or organic bases such as those of alkali metals, for example, sodium and potassium; alkaline earth metals, for example, calcium and magnesium, light metals of group 111 A, for example, aluminum; organic amines such as primary, secondary, or tertiary amines, for example, cyclohexylamine, ethylamine, and pyridine. The salts can be prepared by conventional means such as my contacting and neutralizing a solution of a compound of Formula 1 having a carboxylic acid group in a polar solvent with the stoichiometric quantity of a base, for example, sodium hydroxide. Metal salts also include complex salts, that is, metal chelates which may be obtained by the treatment of a thenoylacetic acid ester of Formula 1 with a metalacetate, such as, cupric acetate or zinc acetate, or by the addition of metal salts, such as, calcium or magnesium salts to a thenoylacetic acid of Formula 1.

Pharmaceutically acceptable salts of the compounds of general Formula 1 wherein $R_1$ represents a basic group are those of any suitable inorganic or organic acids. Suitable inorganic acids are, for example, hydrochloric, hydrobromic, sulfuric or phosphoric acids. Suitable organic acids are, for example, carboxylic acid, such as, acetic, propionic, glycolic, lactic, pyruvic, malonic, succinic, fumaric, malic, tartaric, citric, ascorbic, maleic, hydroxymaleic, benzoic, hydroxybenzoic, phenylacetic, cynnamic, salicylic, and 2-phenoxybenzoic, or sulfonic acid, such as, methane sulfonic, and 2-hydroxyethane sulfonic.

The compounds described herein can exist in both the keto form as represented by general Formula 1 and in the enol form as represented by the following general Formula 11 wherein R, Y and $R_1$ have the meanings defined hereinbefore.

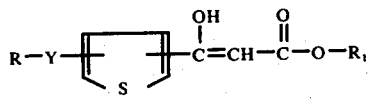

Formula II

For purposes of uniformity the illustrative compounds and specific examples of the compounds defined herein are named as the keto form, that is, the form represented by general Formula 1.

A preferred embodiment of this invention is the compound of the following general Formula 111 and their use as hypolipidemic agents.

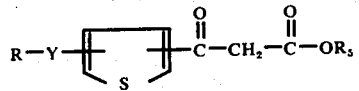

Formula III

In the above Formula 111, the substituents R and Y have the meanings defined in general Formula 1, and $R_5$ is selected from hydrogen, a straight or branched lower alkyl chain of from 1 to 6 carbon atoms, benzyl, and phenethyl; and pharmaceutically acceptable salts of the compounds wherein $R_5$ represents hydrogen.

Another preferred embodiment of this invention is the compounds of the following general Formula IV and their use as hypolipidemic agents.

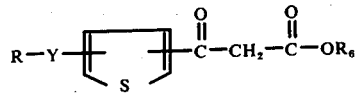

Formula IV

In the above Formula IV, the substituents R and Y have the meanings defined in general Formula 1, and $R_6$ is selected from pyridylmethyl and Z, wherein Z has the meaning defined in general Formula 1; and pharmaceutically acceptable acid addition salts thereof.

A more preferred embodiment of this invention is the compounds of general Formulas III and IV wherein the R—Y— substituent group is attached to the 5-position of the thiophene ring, and the β-oxopropionic acid function is attached to the 2-position of the thiophene ring, that is, compounds of the following general Formulas V and VI wherein the substituent groups have the meanings defined in general Formulas III and IV.

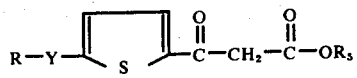

Formula V

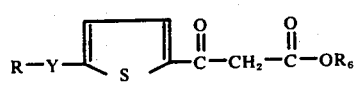

Formula VI

Illustrative examples of compounds of this invention are, for example, 5-decyloxythen-2-oylacetic acid, 5-tetradecyloxythen-2-oylacetic acid methyl ester, 5-(cis-9-octadecenyloxy)-then-2-oylacetic acid ethyl ester, 5-dodecyloxythen-4-oylacetic acid benzyl ester, 5-tetradecyloxythen-3-oyl acetic acid ethyl ester, 5-octadecyloxythen-2-oylacetic acid propyl ester, 5-tetradecylthiothen-3-oylacetic acid butyl ester, 3-tridecyloxythen-2-oylacetic acid benzyl ester, 5-hexadecyloxythen-2-oyl acetic acid methyl ester, 5-heptadecyloxythen-2-oylacetic acid butyl ester, 4-undecylthiothen-4-oylacetic acid ethyl ester, 5-hexadecyloxythen-2-oyl acetic acid diethylamino ethyl ester, 5-pentadecylthiothen-2-oylacetic acid 3-pyridylmethyl ester, 5-hexadecylthiothen-2-oyl acetic acid methyl ester, 4-decyloxythen-2-oylacetic acid, 5-undecyloxythen-2-oylacetic acid ethyl ester, 5-nonadecyloxythen-2-oylacetic acid phenethyl ester, 5-didecyloxythen-3-oylacetic acid propyl ester, 4-didecyloxythen-2-oylacetic acid 4-pyridylmethyl ester, 3-dodecylthiothen-2-oylacetic acid di-propylamino propyl ester, 5-tetradecyloxythen-2-oylacetic acid piperidino ethyl ester, 4-hexadecyloxythen-3-oylacetic acid morpholino ethyl ester, 5-undecyloxythen-2-oylacetic acid 4-(N-methyl)piperidyl ester, 5-(cis-9,12-octadecadienyloxy)then-2-oylacetic acid methyl ester, 5-(3,7-dimethyl-oct-6-enyloxy)then-2-oylacetic acid ethyl ester, 5-tetradecyloxythen-2-oylacetic acid, 5-pentadecyloxythen-2-oylacetic acid, 5-hexadecyloxythen-3-oylacetic acid, 2-tetradecyloxythen-4-oyl acetic acid, 4-tetradecyloxythen-2-oylacetic acid, 5-(9,12,15-octadecatrien-1-yloxy)then-2-oyl acetic acid, 5(3,7,11-trimethyldodecyloxy)then-2-oyl acetic acid, and 5-(3,7,11-trimethyldodecyloxy)then-2-oyl acetic acid 2-dimethylamino ethyl ester.

The compounds of this invention are useful as hypolipidemic agents in that they reduce blood lipids, particularly cholesterol and triglycerides without concurrent accumulation of desmosterol. These compounds can be administered to animals, mammals, rats, dogs, cats, pigs, cows, horses, sheep, and humans and are useful in the treatment of hyperlipidemic states such as are encountered in patients with cardiovascular diseases that can result in heart failure and stroke. As used herein, the term patient is intended to mean the animal or mammal being treated.

The compounds described herein can be administered orally or parenterally either alone or in the form of pharmaceutical preparations. Pharmaceutical preparations containing conventional pharmaceutical carriers and as active ingredients compounds described herein can be employed in unit dosage forms, such as solids, for example, tablets, capsules and pills, or liquid solutions, suspensions, or emulsions for oral and parenteral administration. The quantity of compounds administered can vary over a wide range to provide from about 0.5 mg/kg (milligram per kilogram) to about 300 mg/kg of body weight of the patient per day, and preferably from about 20 mg/kg to 30 mg/kg of body weight of the patient per day, to achieve the desired effect. Unit doses can contain from about 50 mg to 1 g of a compound of this invention and may be administered, for example, from 1 to 4 times daily.

The compounds of general Formula 1 wherein $R_1$ is hydrogen may be prepared by reacting an appropriately R—Y— substituted thiophene methyl ketone with magnesium methyl carbonate in dimethylacetamide or dimethylformamide followed by treatment of the resulting complex with water and a mineral acid, such as, hydrochloric acid. The reaction to obtain the complex may be carried out at temperatures of from −30° C to 50° C and preferably from −20° C to about 25° C. The reaction time varies from about ½ hour to about 3 days depending upon the reactants and temperature of the reaction.

The R—Y— substituted thiophene methyl ketones employed in the above-described reaction may be prepared by the reaction of methyl magnesium bromide and the imidazolide derivative of an appropriately R—Y— substituted thiophenecarboxylic acid or by a Friedel-Crafts acylation of an appropriately R—Y— substituted thiophene with an acyl halide, such as acetyl chloride or acetyl bromide, or acetic anhydride in the presence of an acid catalyst, for example, boron trifluoride-etherate, stannic chloride, zinc chloride, hydriodic acid, or orthophosphoric acid, and optionally in the presence of a solvent, for example, methylene chloride, nitromethane, and benzene. The imidazolide derivative is obtained by treating an appropriately R—Y— substituted thiophenecarboxylic acid with N,N'-carbonyldiimidazole or by treatment of the R—Y— substituted thiophenecarboxylic acid chloride, obtained by treating the substituted thiophenecarboxylic acid with thionyl chloride, with two equivalents of imidazole as generally described by H. A. Staab, Angew. Chem. Internat. Edit. 1, 351(1962).

The appropriately R—Y— substituted thiophenecarboxylic acids are prepared by the reactions on an alcohol or a thioalcohol of the formula R—YH wherein R and Y have the meanings defined in general Formula 1 with bromothiophenecarboxylic acid under basic conditions followed by acidification. The R—Y— substituted thiophene derivatives wherein Y is sulfur can be prepared as described by E. Profft, Chemiker-Zeitung, 82, 298(1958). The R—Y— substituted thiophene derivatives wherein Y is oxygen can be prepared by the reactions of 3-thiolen-2-one [R. T. Hawkins, J. Heterocyclic Chem., 11, 291–4(1974)] with a suitable alkyl halide, alkyl mesylate, or alkyl tosylate in the presence of a base, for example, sodium hydride, potassium amide, potassium tert-butylate, sodium or potassium methyl, potassium carbonate, sodium carbonate, triethylamine, or pyridine, and optionally in the presence of a solvent, for example, pyridine, benzene, xylene, chlorobenzene, ethers, for example, bis(2-methoxyethyl)ether or anisole, dimethylformamide, dimethylacetamide, and hexamethylphosphoric triamide. The alkyl halide employed in this reaction may be, for example, alkyl chloride, alkyl bromide, or alkyl iodide. The alkyl moiety in the alkyl halide, alkyl mesylate or the or the alkyl tosylate employed in this reaction is a hydrocarbon chain containing from 10 to 20 carbon atoms which may be straight or branched and which may be saturated or unsaturated containing from 1 to 4 double bonds.

The R—Y— substituted thiophene methyl ketone may also be prepared by treatment of the corresponding carboxylic acid with methyllithium as generally described by Fieser and Fieser *Reagents for Organic Synthesis*, J. Willy and Sons, Inc., New York, p. 688 (1967).

The 2-(5-R-Y-substituted)-thiophenecarboxylic acids used herein may also be prepared by metalation of the 2-R-Y-thiophene with for example, butyllithium, sodium methyl, diethylmercury, ethyl magnesium chloride, and sodium amalgam, followed by treatment of the reaction mixture with carbon dioxide that is, dry ice, and subsequent acidification with for example hydrochloric acid.

The R—Y— substituted thenoylacetic acids obtained as described hereinabove may be converted to the esters of this invention, that is, compounds of general Formula 1 wherein $R_1$ is other than hydrogen, by treating the acid derivative with trifluoroacetic anhydride, N,N'-dicyclohexylcarbodiimide, N,N'-carbonyldiimidazole, or a thionyl halide, such as, thionyl chloride, followed by alcoholysis of a compound of the formula $R_1OH$ wherein $R_1$ has the meaning defined in general Formula 1 except that it is not hydrogen.

The R—Y— substituted thenoylacetic acids may also be reacted with diazomethane to give the corresponding methyl ester, which may be converted to the esters of higher boiling alcohols of this invention by a standard transesterification reaction with an alcohol of the formula $R_1OH$ wherein $R_1$ has the meaning defined in general Formula 1 except that it is not hydrogen or methyl.

Compounds of general Formula 1 wherein $R_1$ is other than hydrogen may also be prepared by condensing a compound of the formula

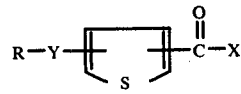

Formula VII wherein R and Y have the meanings defined hereinbefore, and X represents halogen, 1-imidazole or $OR_7$ wherein $R_7$ represents lower alkyl with either an ester of acetoacetic acid followed by alkaline hydrolysis of the resulting thenoylacetoacetate or an ester of acetic acid employing a basic catalyst. These compounds may also be obtained by the acylation of a compound of Formula VII wherein X represents halogen or 1-imidazole with a magnesium complex of malonic acid mono ester of the following general Formula VIII by the method of R. E. Ireland and J. A. Marshall, J. Am. Chem. Soc. 81, 2907 (1959).

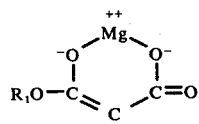

Formula VIII

In the above general Formula VIII $R_1$ has the meaning defined in general Formula 1, except that it is not hydrogen. This reaction is carried out in a solvent such as tetrahydrofuran, dimethylformamide or dimethylacetamide followed by acid hydrolysis with a mineral acid, such as, hydrochloric acid or with ammonium chloride.

The following specific examples are illustrative of the invention.

EXAMPLE 1

5-Tetradecyloxythen-2-oylacetic acid

A mixture of 214 g (1.0 mole) of 1-tetradecanol, 59 g (1.46 mole) of sodium hydride (59.5% in oil) and 31. of dried xylene is heated to reflux with stirring for two hours, then allowed to cool after which 75 (0.46 mole) of 5-chloro-2-thiophene carboxylic acid is added. The mixture is refluxed for 64 hours after which it is cooled and poured into a water:ice mixture, acidified with acetic acid and extracted with the addition of ether. The ether is evaporated, and the xylene layer extracted five times with water:strong ammonia solution (1:1). The combined aqueous extract is acidified with acetic acid. The solution obtained is crystallized twice from hexane to give 2-(5-tetradecyloxy)thiophene carboxylic acid, m.p. 95–96° C.

A mixture of 86.1 g (0.253 mol) of 2-(5-tetradecyloxy)-thiophene carboxylic acid, 41.0 g (0.253 ) of N,N'-carbonyldiimidazole and tetrahydrofuran, is stirred at room temperature during which time carbon dioxide is evolved, and the cooled to give N-[5-(tetradecyloxy)-2-thenoyl]imidazole. The N-substituted imidazole 52.3 g (0.134 mole) in tetrahydrofuran is cooled in an ice bath. An equivalent amount of methyl magnesium bromide (50 ml of a 3 molar solution of ether) is slowly added over two hours to the stirred mixture. The reaction is stirred for an additional hours, then excess (500 ml) of 2N HCl is added and the product extracted into ether. The ether layer is separated, washed with water, dried over sodium sulfate, filtered, and evaporated to dryness to give 5-( tetradecyloxy)-2-thienyl methyl ketone.

The mixture of magnesium methyl carbonate and dimethyl formamide (300 g of a 2.0mM/g solution) is heated in a 120° C oil bath with stirring under carbon dioxide flushing for ½ hour. To this mixture is added 33.8 (0.100 mole) of 5-(tetradecyloxy)-2-thienyl methyl ketone, and the oil bath temperature is raised to 130° C to 150° C. Dry nitrogen is flushed through the mixture for 5 hours. The mixture is allowed to cool at room temperature under carbon dioxide flushing after which it is poured slowly into 3 liters of concentrated HCl -ice (1:1) with vigorous stirring. When the evolution of gas is complete, the precipitate is collected and washed with cold water, then dried to give 5-tetradecyloxythen-2-oylacetic acid.

EXAMPLE 2

5-Tetradecyloxythen-2-oylacetic acid methyl ester

To a cooled suspension of 10.0 g (0.027 mole) of 2-(5-tetradecyloxy)thenoylacetic acid in 500 ml of anhydrous ether is added 0.1 of diazomethane prepared by the method of S. Arndt, Org. Syn. Coll. 2, 165 (1943) in 200 ml of ether, followed by 1.0 ml of boron trifluoride-etherate. The mixture is allowed to stand overnight at room temperature after which it is poured into iced water. The ether layer is separated, washed with water, dried over sodium sulfate, filtered and evaporated to dryness to give 5-tetradecyloxythen-2-oylacetic acid methyl ester.

EXAMPLE 3

5-(Cis-9-octadecenyl-1-yloxy)then-3-oylacetic acid methyl ester

When in Example 1, cis-9-octadecanol is substituted for 1-tetradecanol, and 3-(5-bromo)thiophene carboxylic acid is substituted for 2-(5-chloro)thiophene carboxylic acid, 3-[5-(cis-9-octadecenyloxy)]thiophene carboxylic acid is obtained.

To a cooled mixture of 40.0 g (0.106 mole) of 3-[5-(cis-9-octadecenyloxy)]thiophene carboxylic acid in methylene chloride is added 30 ml of thionyl chloride. The mixture is stirred for five hours after which the solid and excess thionyl chloride are removed under reduced pressure affording the crude 3-[5-(cis-9-octadecenyloxy)]thenoyl chloride. A mixture of 11.6 g (0.100 mole) of methylacetoacetate and 2.3 g of sodium in one liter of benzene is refluxed for 20 hours, cooled and the crude 3-[5-(cis-9-octadecenyloxy)]-thenoyl chloride is added over a two hour period. The mixture is refluxed for six hours, cooled by the addition of ice and mixed well. The benzene layer is separated, washed with 5% sodium bicarbonate solution and dried. The benzene is distilled off under reduced pressure yielding 3-[5-(cis-9-octadecenyloxy)-3-thenoyl-]acetoacetic acid methyl ester. To a solution of 3.3 g of ammonium chloride and 15 ml of water at 40' C is added 10 g of the above ester maintaining the temperature at 40' C for 15 minutes followed by rapid cooling. The solution is extracted with ether, the extract dried and evaporated to dryness to give 5-(cis-9-octadecenyloxy)then-3-oylacetic acid methyl ester.

EXAMPLE 4

5-Tetradecylthiothen-2-oylacetic acid

A mixture of 18.6 g (0.090 mole) of 2-(5-bromo)thiophene carboxylic acid, 25.0 g (0.109 mole) of 1-tetradecanethiol and 500 ml of dried dimethylacetamide is stirred at room temperature after which 10.8 g (0.200 mole) of sodium methoxide is added. The mixture is heated, and the methanol is formed is allowed to spill off. The mixture is refluxed for 24 hours after which the mixture is cooled and poured into a water-ice mixture, acidified with 10% aqueous hydrochloric acid, filtered and the precipitate washed with water and dried. The solid obtained is crystallized from methanol then recrystallized from hexane to give 2-(5-tetradecylthio)thiophene carboxylic acid, M. P. 106°–108° C.

To 17.8 g (0.05 mole) of 2-(5-tetradecylthio)thiophene carboxylic acid in tetrahydrofuran cooled in an ice bath is added 3.3 g (0.15 mole) of methyl lithium. The mixture is allowed to warm up to room temperature, then treated with saturated ammonium chloride solution until neutral to litmus paper to give 5-(tetradecylthio)-2-thienylmethyl ketone.

When in Example 1 an appropriate amount of 5-(tetradecylthio)-2-thienylmethyl ketone is substituted for 5-(tetradecyloxy)-2-thienylmethyl ketone, 5-tetradecylthiothen-2-oylacetic acid is obtained.

EXAMPLE 5

5-Tetradecylthiothen-2-oylacetic acid benzyl ester 7.0 g (0.02 mole) of 2-(5-tetradecylthio)thenoylacetic acid is suspended in anhydrous ether and cooled in an ice bath. To this suspension is added 12.6 g (0.06 mole) of trifluoroacetic anhydride, and the mixture is allowed to stand at room temperature for one hour after which 6.5 g (0.66 mole) of benzyl alcohol is added. The mixture is stirred at room temperature for one hour then evaporated to dryness under reduced pressure to give 5-tetradecylthiothen-2-oylacetic acid benzyl ester.

EXAMPLE 6

5-)9,12,15-Octadecatrien-1-yloxy)then-2-oylacetic acid ethyl ester

A mixture of 20.0 g (0.2 mole) of 3-thiolen-2-one [R. T. Hawkins, J. Heterocyclic Chem., 11 291–4 (1974)9 65.5 g (0.2 mole) of 1-bromo-9,12,15-octadecatriene, and 4.8 g (0.2 mole) of sodium hydride in benzene is refluxed with stirring for 24 hours after which the solvent is removed, and the product distilled to give 2-(9,12,15-octadecatrienyloxy)thiophene.

To 6.0 g of sodium amalgam in 100 ml of anhydrous ether at reflux temperature 36°–39° C) under slight nitrogen pressure is added 34.7 g (0.10 mole) of 2-(9,12,15-octadecatrienyloxy)thiophene in 50 ml of anhydrous ether over a four hour period. The mixture is refluxed an additional two hours. The mixture is cooled to room temperature and carbonated by adding freshly crushed dry ice after which 20 ml of ethanol is added dropwise followed by the addition of 50 ml of water. The aqueous solution is separated from the ether layer, filtered and acidified with hydrochloric acid to precipitate 5-(9,12,15-octadecatrien-1-yloxy)-2-thiophene carboxylic acid.

To 36.3 g (0.10 mole) of 5-(9,12,15-octadecatrien-1-yl-oxy)-2-thiophene carboxylic acid in anhydrous tetrahydrofuran is added 17.4 g (0.107 mole) of N,N'-carbonyldiimidazole. The mixture is stirred at room temperature until the evolution of carbon dioxide gas ceases after which the mixture is evaporated to dryness, and the residue extracted with anhydrous ether. The ether extract is evaporated to dryness to give N-[5-(9,12,15-octadecatrien-1-yloxy)-2-thenoyl]imidazole.

A mixture of 14.5 g (0.110 mole) of malonic acid mono ethyl ester, 19.0 g (0.220 mole) of magnesium methoxide and anhydrous tetrahydrofuran is heated with stirring under nitrogen allowing the methanol produced to distill off. To this mixture is added 45.0 g (0.105 mole) of N-[5-(9,12,15-octadecatrien-1-yloxy)-2-thenoyl]imidazole with stirring and cooling on an ice bath for four hours. The solvent is removed and the residue diluted with ice-concentrated HCl (1:1) solution to give 5-(9,12,15-octadecatrien-1-yloxy)then-2-oylacetic acid ethyl ester.

EXAMPLE 7

5-Tetradecyloxythen-2-oylacetic acid benzyl ester

A mixture of 10.4 g (0.027 mole) of 2-(5-tetradecyloxy)thenoylacetic acid, 4.4g (0.027 mole) of N,N'-carbonyldiimidazole, and anhydrous tetrahydrofuran is stirred until the evolution of carbon dioxide gas stops. The mixture is cooled on an ice bath, in 3.0 g (0.027 mole) of benzyl alcohol is added. The reaction is allowed to warm to room temperature and evaporated to dryness. Theresidue is extracted with ether-H₂O. The ether layer is washed with 10% aqueous HCl, then water, then saturated sodium chloride, dried with sodium sulfate and evaporated to dryness to give 5-tetradecyloxythen-2-oylacetic acid benzyl ester.

EXAMPLE 8

5-Dodecylthiothen-2-oylacetic acid

When in Example 1, 1-dodecanethiol is substituted for 1-tetradecenol, 5-dodecylthiothen-2-oylacetic acid is obtained.

EXAMPLE 9

5-Dodecylthiothen-2-oylacetic acid 2-acetamido ehtyl ester

A mixture of 20.9 g (0.057 mole) of 2-(5-dodecylthio)-thenoylacetic acid, 9.2 g (0.057 mole) of N,N'-carbonyldiimidazole and tetrahydrofuran is stirred for 4 hours after which 5.9 g (0.057 mole) of N-acetylethanolamine is added. The mixture is stirred at room temperature overnight, and is diluted with ice cold 5% aqueous hydrochloric acid and extracted with ether. The ether layer is washed in water and saturated sodium chloride solution, dried with sodium sulfate and evaporated to dryness to yield 5-dodecylthiothen-2-oylacetic acid 2-acetamido ethyl ester.

EXAMPLE 10

5-(3,7,11-trimethyldodecyloxy)then-2-oylacetic acid 2-dimethylamino ethyl ester and the hydrochloride salt When in Example 1 an appropriate amount of 3,7,11-trimethyl-1-dodecanol is substituted for 1-tetradecanol, 2-[5-(3,7,11-trimethyldodecyloxy)]-thenoylacetic acid is obtained. This acid is combined with an equimolar amount of N,N'-carbonyldiimidazole and b 2-dimethylamino ethanol in anhydrous tetrahydrofuran after which the solvent is removed under reduced pressure, and the residue is extracted with etherwater. The ther layer is evaporated to dryness to give 2-5-(3,7,11-trimethyldodecyloxy)]-thenoylacetic acid 2-dimethylamino ethyl ester. By dissolving 2[5-(3,7,11-trimethyldodecyloxy)]thenoylacetic acid 2-dimethylamino ethyl ester in ether followed by treatment of the solution with one equivalent of HCl gas and collecting the precipitate gives 2-5-(3,7,11-trimethyldodecyloxy)then-2-oylacetic acid 2-diethylamino ethyl ester hydrochloride.

EXAMPLE 11

An illustrative composition for tablets is as follows:

|     |                                                           | Per Tablet |
| --- | --------------------------------------------------------- | ---------- |
| (a) | 5-(tetradecyloxy)-2-then-2-oyl-acetic acid methyl ester  | 100.0 mg   |
| (b) | wheat starch                                              | 15.0 mg    |
| (c) | lactose                                                   | 33.5 mg    |
| (d) | magnesium stearate                                        | 1.5 mg     |

A portion of the wheat starch is used to make a granulated starch paste which together with the remainder of the wheat starch and the lactose is granulated, screened and mixed with the active ingredient (a) and the magnesium stearate. The mixture is compressed into tablets weighing 150 mg each.

EXAMPLE 12

An illustrative composition for a parenteral injection is the following wherein the quantities are on a weight to volume basis.

|     |                                                                                             | Amount |
| --- | ------------------------------------------------------------------------------------------- | ------ |
| (a) | 5-(3,7,11-trimethyldodecyloxy)-2-then-2-oylacetic acid 2-diethyl-aminoethyl ester hydrochloride | 100.0 mg |
| (b) | sodium chloride                                                                             | q.s.   |
| (c) | water for injection to make                                                                 | 20.0 ml |

The composition is prepared by dissolving the active ingredient (a) and sufficient sodium chloride in water for injection to render the solution isotonic. The composition may be dispensed in a single ampule containing 100 mg of the active ingredient for multiple dosage or in 20 ampules for single dosage.

EXAMPLE 13

An illustrative composition for hard gelatin capsulses is as follows:

|     |                                         | Amount |
| --- | --------------------------------------- | ------ |
| (a) | 5-(tetradecyloxy)then-2-oylacetic acid methyl ester | 200.0 mg |
| (b) | talc                                    | 35.0 mg |

The composition is prepared by passing the dry powders of (a) and (b) through a fine mesh screen and mixing them well. The powder is then filled into No. 0 hard gelatin capsules at a net fill of 235 mg per capsule.

EXAMPLE 14

When in the procedure of Example 1 an appropriate amount 4-chloro-3-thiophene carboxylic acid or 4-chloro-2-thiophene carboxylic acid the following compounds are obtained: 4-tetradecyloxythen-3-oylacetic acid; and 4-tetradecyloxythen-2-oylacetic acid.

I claim:

1. A compound selected from the formula:

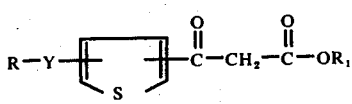

wherein Y is selected from oxygen and divalent sulfur; R is selected from a straight or branched saturated hydrocarbon chain containing from 10 to 20 carbon atoms and a straight or branched unsaturated hydrocarbon chain containing from 10 to 20 carbon atoms and from 1 to 4 double bonds; $R_1$ is selected from hydrogen, a straight or branched lower alkyl chain of from 1 to 6 carbon atoms, benzyl, phenethyl, and the group

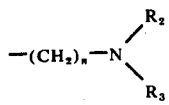

wherein $n$ is the integer 2 or 3; $R_2$ is selected from a straight or branched lower alkyl chain of from 1 to 4 carbon atoms; $R_3$ is selected from hydrogen and a straight or branched lower alkyl chain of from 1 to 4 carbon atoms with the proviso that when $R_3$ is hydrogen, $R_2$ is alkylcarbonyl and pharmaceutically acceptable salts thereof.

2. A compound of claim 1 wherein $R_1$ is selected from hydrogen, a straight or branched lower alkyl chain of from 1 to 6 carbon atoms, benzyl, and phenethyl; and pharmacetically acceptable salts thereof.

3. A compound of claim 2 wherein Y is oxygen.

4. A compound of claim 2 wherein Y is divalent sulfur.

5. A compound selected from the formula:

wherein Y is selected from oxygen and divalent sulfur; R is selected from a straight or branched saturated hydrocarbon chain containing from 10 to 20 carbon atoms and a straight or branched unsaturated hydrocarbon chain containing from 10 to 20 carbon atoms and from 1 to 4 double bonds; $R_5$ is selected from hydrogen, a straight or branched lower alkyl chain of from 1 to 6 carbon atoms, benzyl, and phenethyl; and pharmaceutically acceptable salts thereof.

6. A compound of claim 5 wherein Y is oxygen.

7. A compound of claim 5 wherein R is selected from a straight or branched saturated hydrocarbon chain containing from 12 to 16 carbonatoms and a straight or branched unsaturated hydrocarbon chain containing from 12 to 16 carbon atoms and from 1 to 4 double bonds.

8. A compound of claim 7 which is 2-(5-tetradecyloxy)-thenoylacetic acid and pharmaceutically acceptable salts thereof.

9. A compound of claim 5 wherein Y is divalent sulfur.

10. A compound selected from the formula:

wherein Y is selected from oxygen and divalent sulfur; R is selected from a straight or branched saturated hydrocarbon chain containing fom 10 to 20 carbon atoms and a straight or branched unsaturated hydrocarbon chain containing from 10 to 20 carbon atoms and from 1 to 4 double bonds; $R_6$ is the group

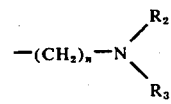

wherein $n$ is the integer 2 or 3; $R_2$ is selected from a straight or branched lower alkyl chain of from 1 to 4 carbon atoms and alkylcarbonyl wherein the alkyl moiety contains from 1 to 4 carbon atoms; $R_3$ is selected from hydrogen and a straight or branched lower alkyl chain of from 1 to 4 carbon atoms with the proviso that when $R_3$ is hydrogen, $R_2$ is alkylcarbonyl; and pharmaceutically acceptable salts thereof.

11. A pharmaceutical composition comprising in unit dosage form from about 50 mg to 1 g of a compound of claim 1 and a significant amount of pharmaceutically acceptable carrier.

12. A method of reducing the lipid concentration in the blood of a patient in need thereof which comprises administering to said patient a lipid lowering effective amount of a compound of claim 1.

* * * * *

UNITED STATES PATENT AND TRADEMARK OFFICE
CERTIFICATE OF CORRECTION

PATENT NO. : 4,032,647

DATED : June 28, 1977

INVENTOR(S) : Roger Alan Parker

It is certified that error appears in the above-identified patent and that said Letters Patent are hereby corrected as shown below:

Column 7, line 10 "...75 (0.46 mole)..." should read --75 g (0.46 mole)--; line 19 "...The solution obtained..." should read --The solid obtained--; line 22 "...(0.253 mol)..." should read --(0.253 mole)---; line 23 "...(0.253)..." should read --(0.253 mole)--; line 26 "...is evolved, and the cooled..." should read --is evolved, then cooled--; line 32 "...an additional hours..." should read --an additional three hours--; line 43 "...is added 33.8 (0.100 mole)..." should read --is added 33.8 g (0.100 mole)--; line 59 "...0.1 of..." should read --0.1 mole of--. Column 8, line 28 "...40'C..." should read --40°C--; line 30 "...40'C..." should read --40°C--; line 42 "...methanol is formed is..." should read --methanol formed is--. Column 9, line 13 "...(1974)9..." should read --(1974)1--; line 20 "...36-39° C)..." should read --(36-39° C)--. Column 10, line 10 "...ehtyl..." should read --ethyl--; line 33 "..b 2 dimethylamino..." should read --2-dimethylamino--; line 37 "...The ther layer..." should read --The ether layer--.

Column 11, line 34, after "acids" insert -- is substituted for 5-chloro-2-thiophene carboxylic acid --; Column 11, line 62, after "atoms" insert -- and alkylcarbonyl wherein the alkyl moiety contains from 1 to 4 carbon atoms --. Column 12, line 41 "...fom.." should read -- from --.

Signed and Sealed this

Twenty-seventh Day of June 1978

[SEAL]

Attest:

RUTH C. MASON
Attesting Officer

DONALD W. BANNER
Commissioner of Patents and Trademarks